(12) United States Patent
Alroy

(10) Patent No.: US 7,374,545 B2
(45) Date of Patent: May 20, 2008

(54) DEVICE FOR SAMPLING BLOOD DROPLETS UNDER VACUUM CONDITIONS

(75) Inventor: Yoram Alroy, Tel Aviv (IL)

(73) Assignee: SHL Telemedicine International, Ltd., Tel-Aviv (IS)

( * ) Notice: Subject to any disclaimer, the term of this patent is extended or adjusted under 35 U.S.C. 154(b) by 268 days.

(21) Appl. No.: 10/496,981

(22) PCT Filed: Jul. 23, 2002

(86) PCT No.: PCT/IL02/00608

§ 371 (c)(1),
(2), (4) Date: May 27, 2004

(87) PCT Pub. No.: WO03/045241

PCT Pub. Date: Jun. 5, 2003

(65) Prior Publication Data

US 2005/0033196 A1    Feb. 10, 2005

(30) Foreign Application Priority Data

Nov. 27, 2001 (IL) ..................................... 146776

(51) Int. Cl.
*A61B 5/00* (2006.01)
(52) U.S. Cl. ...................... 600/583; 600/573; 600/584; 606/181; 606/182
(58) Field of Classification Search ................ 600/584, 600/573; 604/335, 317
See application file for complete search history.

(56) References Cited

U.S. PATENT DOCUMENTS

| | | |
|---|---|---|
| 3,634,039 A | 1/1972 | Brondy |
| 3,724,455 A | 4/1973 | Unger |
| 4,004,577 A | 1/1977 | Sarnoff |
| 4,261,388 A | 4/1981 | Shelton |
| 4,396,023 A | 8/1983 | Anderson |
| 4,493,710 A | 1/1985 | King et al. |
| 4,661,319 A * | 4/1987 | Lape ........................... 422/100 |
| 4,712,562 A | 12/1987 | Ohayon et al. |
| 4,876,203 A * | 10/1989 | Guigan ......................... 436/45 |
| 5,007,429 A | 4/1991 | Treatch et al. |
| 5,035,865 A | 7/1991 | Inaba et al. |
| 5,109,866 A * | 5/1992 | Guegan et al. ............. 600/368 |
| 5,320,607 A | 6/1994 | Ishibashi |
| 5,951,492 A * | 9/1999 | Douglas et al. ............. 600/583 |
| 6,071,251 A | 6/2000 | Cunningham et al. |
| 6,099,484 A * | 8/2000 | Douglas et al. ............. 600/583 |
| 6,104,940 A * | 8/2000 | Watanabe et al. ........... 600/345 |
| 6,295,506 B1 * | 9/2001 | Heinonen et al. ........... 702/104 |
| 6,306,104 B1 * | 10/2001 | Cunningham et al. ....... 600/573 |

(Continued)

FOREIGN PATENT DOCUMENTS

WO    WO 01/52727 A1    7/2001

*Primary Examiner*—Max Hindenburg
*Assistant Examiner*—H. Q. Nguyen
(74) *Attorney, Agent, or Firm*—Browdy and Neimark

(57) ABSTRACT

A blood extraction device (100) and method for withdrawing a controlled number of drops of blood from a patient, in whom there is created an incision of such dimension that blood does not freely flow therefrom. A release unit (160) urges drops of blood to flow from the incision, for example by applying a vacuum, and a disabling unit (145, 146, 170) is coupled to the incision unit for disabling the release unit when a predetermined number of drops of blood have been withdrawn.

10 Claims, 4 Drawing Sheets

U.S. PATENT DOCUMENTS

| | | |
|---|---|---|
| 6,511,814 B1 * | 1/2003 | Carpenter .................. 435/7.21 |
| 2001/0011224 A1 | 8/2001 | Brown |
| 2002/0123671 A1 * | 9/2002 | Haaland ..................... 600/300 |

* cited by examiner

DEVICE FOR SAMPLING BLOOD DROPLETS UNDER VACUUM CONDITIONS

FIELD OF THE INVENTION

This invention relates to blood sampling and analysis.

BACKGROUND OF THE INVENTION

It has been a long-standing goal in the health care community to integrate advanced communications systems with information processing systems to provide superior medical services. Various devices have been developed that enable medical data to be obtained for improving the monitoring of medical conditions of patients thus providing an earlier warning of possible distress.

By way of example, U.S. Pat. No. 4,004,577 discloses a method for treating coronary-prone patients when heart attack symptoms occur before qualified direct contact personal care can be administered. In this patent, a device provides auditory signals indicative of the existing heartbeat, and telephone communication is established between the patient and a remote center, capable of making a qualified response based on the auditory signals.

Another example is U.S. Pat. No. 4,712,562, that discloses a system and method for obtaining from a patient's body information pertaining to the patient's blood pressure and heart rate, and generates signals representative thereof in a form suitable for telephonic communication, and transmits these signals to a remote central digital processor for storage and analysis. The data resulting from the analysis is submitted to the patient or physician. Similar systems are disclosed in U.S. Pat. Nos. 3,724,455 and 5,007,429. All of the above patents disclose non-invasive measurements that are to be performed at home (typically by the patient himself). The scope of medical information that can be thus gathered from a patient and transmitted to a remote medical center is limited.

Important medical indications can be measured by blood analysis. It is known from U.S. Pat. No. 6,071,251 for example, to monitor levels of Glucose in the blood as an indication of diabetes. For diagnosing various cardiac conditions, particularly damage to the heart muscle, it is known to measure levels of Troponin T, Troponin I and Myoglobin in the blood.

Blood sampling and analyses are usually performed in a hospital or laboratory. Typically, the test is not performed by the patient himself but rather by professional personnel. The blood sample can either be analyzed immediately or, at a later time and at a different location from where it is sampled. Usually blood is drawn by vacuum by means of either a manual or automated process. The test may be performed either in situ or at a remote location.

The use of vacuum for blood extraction is exemplified in U.S. Pat. No. 4,396,023, which discloses an apparatus for obtaining blood samples from the tails of animals, such as mice or rats. The tail is nicked or transected and then placed in a single-use vacuum tube connected to a one-hole rubber stopper. The vacuum is communicated into the interior of the tube via a hole therein and promotes the flow of blood from the tail. When the desired volume of blood has been collected, the vacuum is turned off and the animal is removed.

The use of a vacuum for blood extraction is also exemplified in U.S. Pat. No. 5,320,607, which discloses a leech-like skin-adhesive blood sampling device comprising a sealed vacuum chamber in a state of pre-existing reduced pressure, a piercing means and means for collecting the drawn blood. However, this patent does not disclose the possibility to control the operation of the device in accordance with the quantity of the drawn blood.

In several patents to Abbot Laboratories, particularly U.S. Pat. No. 6,071,251 a method and apparatus for obtaining blood for diagnostic testing is disclosed. In the above patent, an opening in the skin is made and a vacuum is used to aid in extracting the sample of blood. The vacuum is applied to the surface of the skin in the vicinity of the opening, causing the site to become engorged with blood and the skin to become more stretched. As a result, the skin rises up to a position where it seals the vacuum chamber, after which it is pricked by a lancet assembly. The blood is then drawn to a strip capable of detecting analytes therein. The detecting strip is positioned near the site of the opening of the skin (no more than a few millimeters), so there is physical contact between the blood extracted and the strip, a minute quantity of blood being absorbed by the chemical strip and diffused through the layers thereof. To this end, a special multi-layer chemical strip must be used and the device is not suitable for use with standard chemical strips, which on the other hand, require a larger quantity of blood, typically several drops (quantities in the range of 150-200 micro-liters of blood) usually sampled in a separate process, by professional personnel. Thus, it would be of advantage, for the purpose of self-sampling and testing of blood, to utilize a common and standard chemical test strip.

U.S. Pat. No. 3,634,039 discloses a blood-testing device that enables a predetermined amount of blood to be withdrawn as a function of the number of tests to be performed. U.S. Pat. No. 5,035,865 discloses a vacuum blood sample-collecting device which includes means for measuring the amount of collected blood in the blood container. Neither patent discloses an apparatus for predetermining or measuring a small quantity of blood, such as a few drops.

U.S. Pat. No. 4,493,710 discloses a drip-rate sensing means which is included in an intravenous drip-rate controller device for use in controlling the drip rate of a solution from an intravenous container into the vein. U.S. Pat. No. 4,261,388 discloses a liquid drip-rate controller including an optical sensor for controlling the flow of fluid from an infusion fluid reservoir to an intravenous infusion site. Neither patent discloses a device capable of counting drops of blood drawn from the vein.

There is a need in the art for a device that would enable a patient to perform a blood test and analysis on his own (or with the help of a non-professional), and that would require withdrawal of only several drops of blood.

SUMMARY OF THE INVENTION

The present invention provides a blood extraction device and method for withdrawing a controlled number of drops of blood from a patient. According to one embodiment of the invention, the device comprises an incision unit for creating an incision in the patient; a release unit for urging blood drops to flow from said incision, and a disabling unit coupled to the incision unit for disabling the release unit; characterized in that:

a collecting receptacle is disposed in spaced relationship with the release unit for collecting discrete drops of blood that freely fall thereon; and the disabling unit is adapted to disable the release unit when a predetermined number of discrete drops of blood have been withdrawn.

According to one aspect of the invention, the device also comprises a chemical test holder constituting a receptacle for receiving a single-use chemical test strip on which the blood drops are gathered. Alternatively, the blood may be collected in the receptacle for subsequent analysis.

The device may also comprise a camera for imaging the chemical test result obtained by the chemical test strip and an electronic circuit coupled to the camera for transmitting the resulting test data to a remote unit.

The invention provides a method for withdrawing a controlled number of drops of blood from a patient, comprising: creating an incision in the patient; urging blood drops to flow from said incision; and inhibiting blood flow; characterized in that:

blood flows from the incision and falls onto a collection receptacle disposed in spaced relationship with the release unit for collecting discrete drops of blood that freely fall thereon; and said inhibiting blood flow is performed when a predetermined number of discrete drops of blood have been withdrawn.

The invention further provides a method for sampling and testing a controlled number of drops of blood from a patient and transmitting the result of the blood test to a remote unit, comprising the steps of: creating in the patient an incision of such dimension that blood does not freely flow therefrom, urging blood drops to flow from said incision, inhibiting blood flow when a predetermined number of drops of blood have been withdrawn, gathering the blood drops on a single use chemical test strip, imaging a test result obtained by the chemical test strip, and transmitting data representative of an image of the result to a remote unit.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
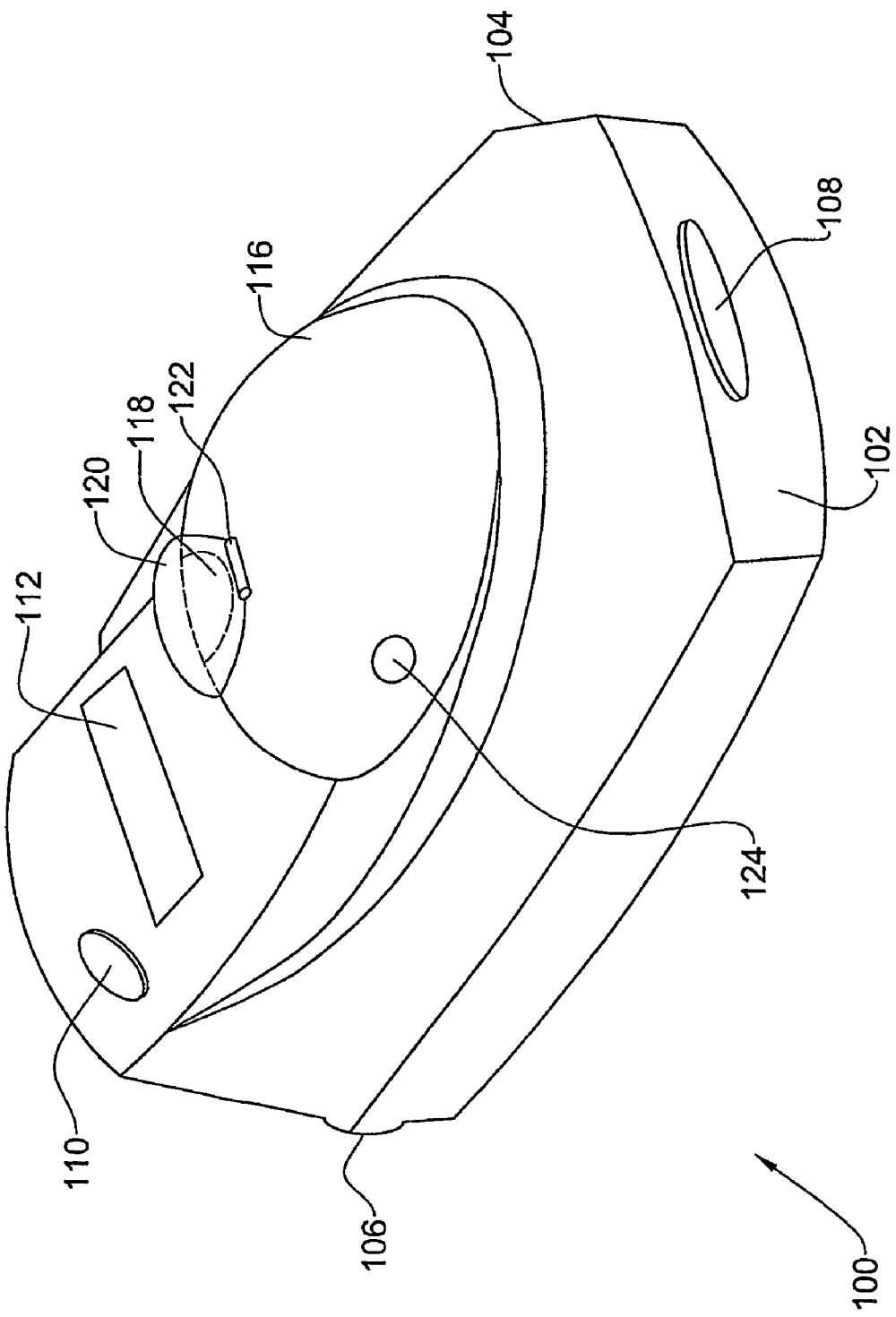
FIG. 1 is a top perspective view of a blood sampling and testing device according to the invention.
Figure 2:
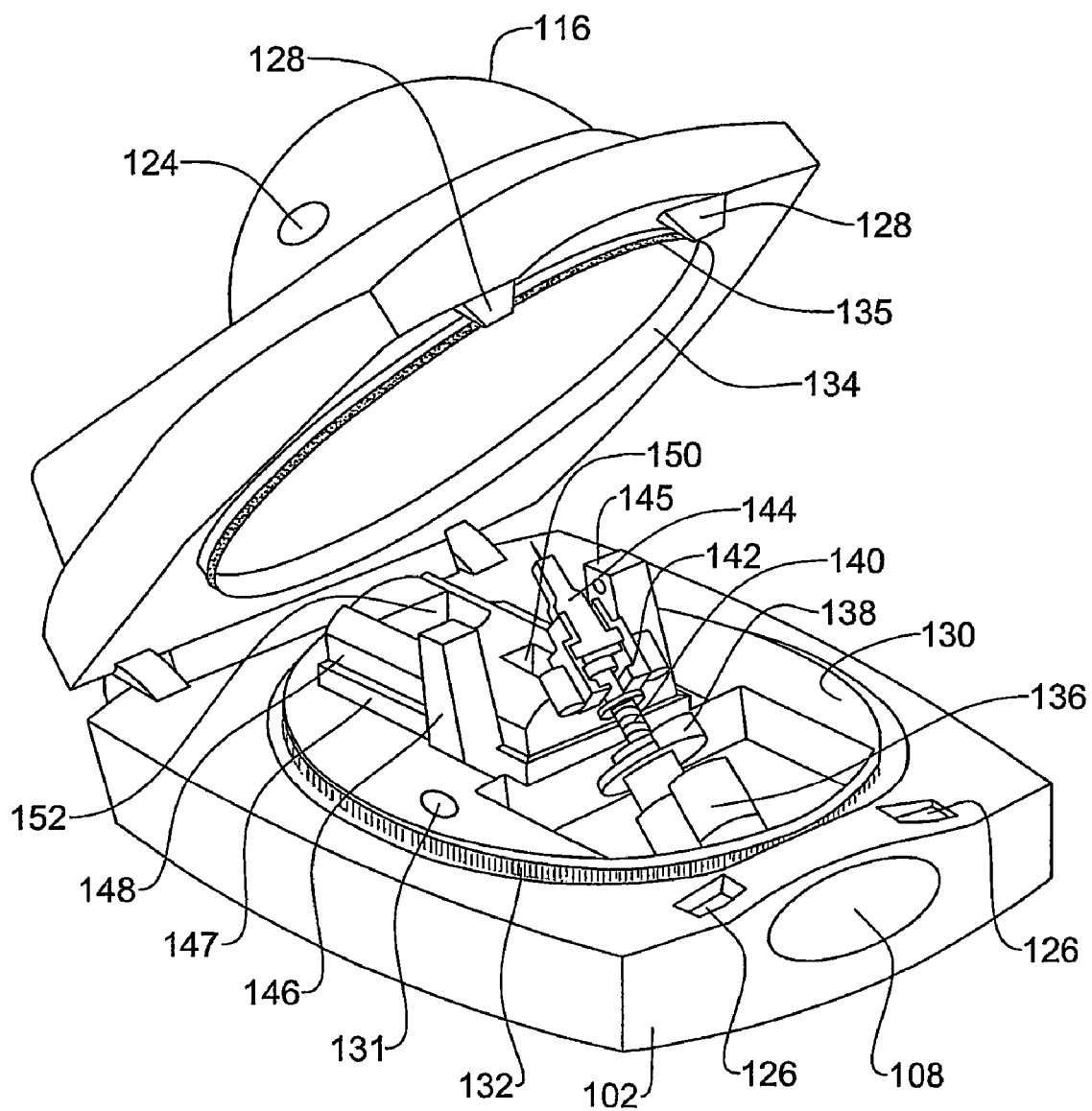
FIG. 2 is a top perspective view of a blood sampling and testing device of FIG. 1 with the cover in "open position"

Reference is first made to FIGS. 1 and 2 showing a blood sampling and testing device 100 according to the invention. The device 100 enables a desired number of drops of blood to be drawn from a patient's finger, (typically 5-6 drops) and performs a desired chemical analysis of the blood by means of an appropriate chemical test strip.

The device 100 comprises a base 102 and a cover 104 pivotally connected to base 102 by a hinge 106. A cover release button 108 is located in the base 102 and a pushbutton actuator 110 and an indicator 112 are located in the cover 104. The indicator 112 may include an LCD display and LED (light emitting diode) and indicates the operational steps performed by the device 100. A canopy 116 forms part of the cover 104. On top of the canopy 116 there are located a finger compartment 118 and a vacuum manual release button 124. The finger compartment 118 is covered by a finger holder 120 that is rotatably connected to the canopy 116 by a hinge 122 and can be lifted to an open position. The finger holder 120 may be resiliently biased so as to exert slight pressure on the patient's finger when inserted into the finger compartment 118.

Reference is now made to FIG. 2 showing a top perspective view of a blood sampling and testing device of FIG. 1, with the cover 104 in the "open position". Snap-holes 126 are located in the base 102 and are connected to the cover release button 108 for accommodating therein clasps 128. A table 130 is located within the base 102 and is surrounded by a channel 132 forming an annular recess for accommodating a sealing edge 134 being the lower part of the canopy 116. Around the outer periphery of the sealing edge 134 is attached an elastic sealing ring 135 made of silicon or the like. When the cover 104 is in its "closed position", the sealing edge 134 and the circumferential elastic sealing ring 135 are sealingly pressed into the channel 132, thus creating a sealed chamber 115 (shown in FIG. 3) within the canopy 116 that is part of the release unit (as described below with reference to FIG. 3). An opening 131 is accessible from the surface of the table 130 and is connected to a vacuum source 160 through tubing 162 shown partially in FIG. 3. The chamber 115 within the canopy 116 can be subjected to a vacuum when the finger compartment 118 is sealed, for example by a patient's finger or other body part. On the table 130, there is located an incision unit which comprises a motor 136, lifting gear 138, spring 140, lancet holder 142 and lancet 144. The motor 136, lifting gear 138 and spring 140 of the incision unit are covered, so that during regular operation only the lancet holder 142 and the lancet 144 can be freely accessed.

Projecting upwardly from the table 130 is a light source 145 that operates in conjunction with an opposing an electro-optical sensor 146 so as to intercept and count drops of blood released from the patient's finger. The light source 145 and the electro-optical sensor 146 are a part of a disabling unit (as will be further described with reference to FIG. 3). Likewise, a chemical test strip holder 147 and a chemical test strip 148 are located on the table 130. The chemical test strip holder 147 constitutes a collecting receptacle for collecting blood droplets and for accommodating therein the chemical test strip 148. The chemical test strip 148 receives blood samples through a sample window 150 and shows the test result visually at a result window 152. The incision unit, the light source 145, the electro-optical sensor 146, and the chemical test strip 148 are spatially arranged with respect to the finger compartment 118 so as to ensure that blood drops extracted from the patient's finger pricked by the lancet 144 fall on to the sample window 150, and upon falling are sensed by the electro-optical sensor 146.

Figure 3:
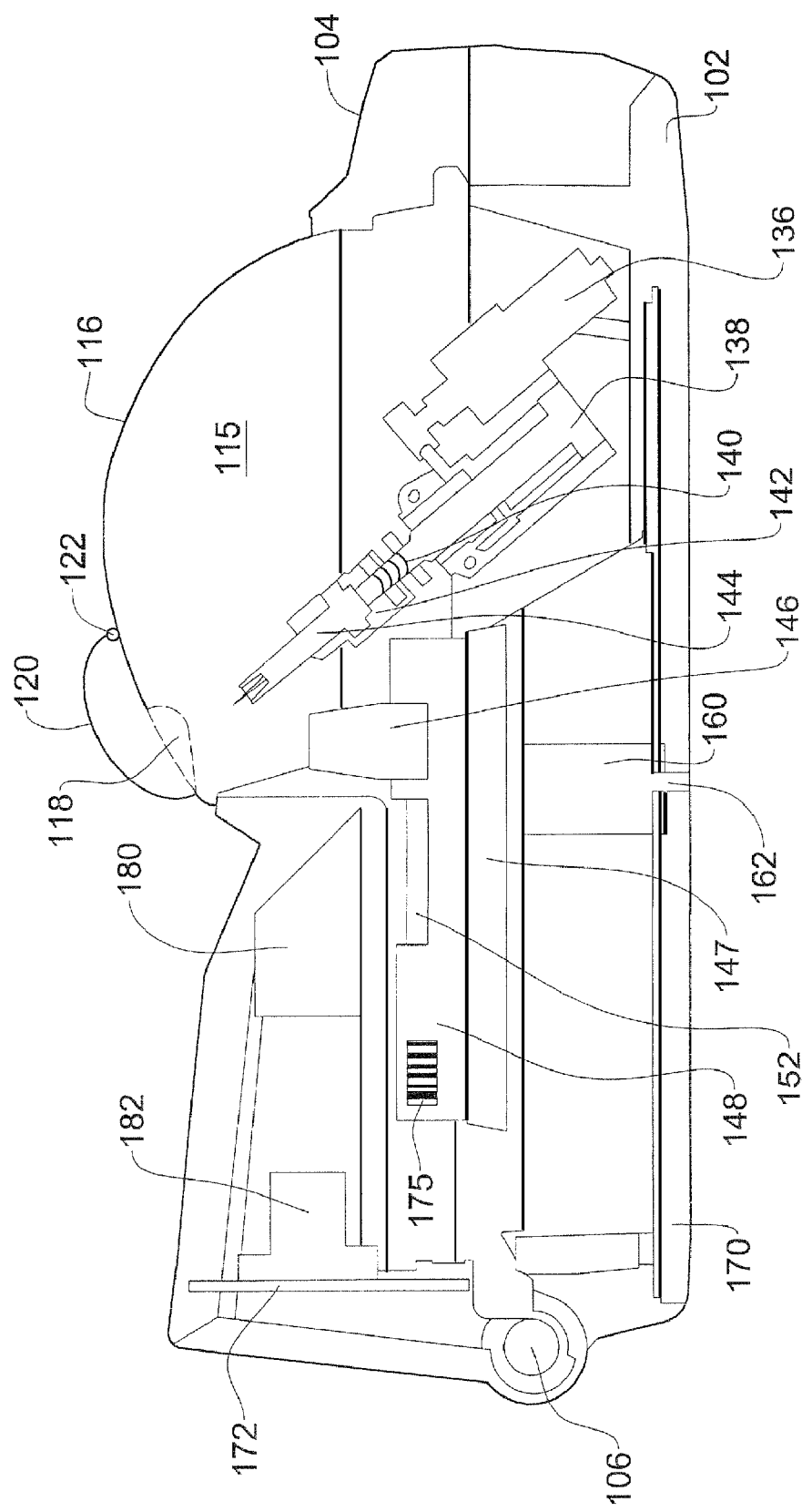
FIG. 3 is a cross-section view of the blood sampling and testing device of FIGS. 1-2.

Further reference is now made to FIG. 3, showing a cross-section view of the blood sampling and testing device 100 in its closed position and showing more particularly the release unit including a vacuum pump 160 coupled to an electronic circuit 170 that is activated by the pushbutton actuator 110. In this embodiment of the invention, the device 100 comprises an internal vacuum source, i.e., vacuum pump 160. However, the device 100 can also be implemented using an external vacuum source connected to the chamber 115 by tubing. The disabling unit comprises the electro-optical sensor 146, the light source 145 and electronic circuit 170. The disabling unit is coupled to the release unit, and can thus release the vacuum and in consequence, cease blood extraction as soon as a desired number of drops are collected.

The device operates from a power source (not shown) that may be disposed within the base 102 or be externally coupled to the device 100.

Also shown in FIG. 3 is an optional lens 180 optically coupled to a camera 182 (constituting an imaging device), for imaging the visual test result appearing at the result window 152 and being connected to the electronic circuit 172 for converting the image to a suitable form and transmitting it to a remote end through an electric connection (not shown). The device 100 may be coupled to another device, which receives the visual test results and transmits them via a telephone line to a remote end to the physician of the tested patient.

In a specific embodiment, the device 100 may be a portable self-test device for a cardiac patient. When using the device, the patient performs a series of preliminary steps for preparing the device, and then operates the device by depressing the pushbutton actuator 110 which activates the device to automatically perform operational steps for sampling and testing freshly drawn blood for blood enzymes that indicate a heart disorder. The results of the analysis may then be transmitted over a telephone line to a remote monitoring station, for allowing remote diagnosis of the patient's medical condition and determining if and what medical action is necessary.

By way of example, the chemical test strip may aim at testing the Myo-globin, Troponin T and Troponin I levels in a patient's blood. However, it should be understood that the device could be used with any other chemical test strip that requires a known and predefined quantity of blood, for any diagnostic purpose.

Figure 4:
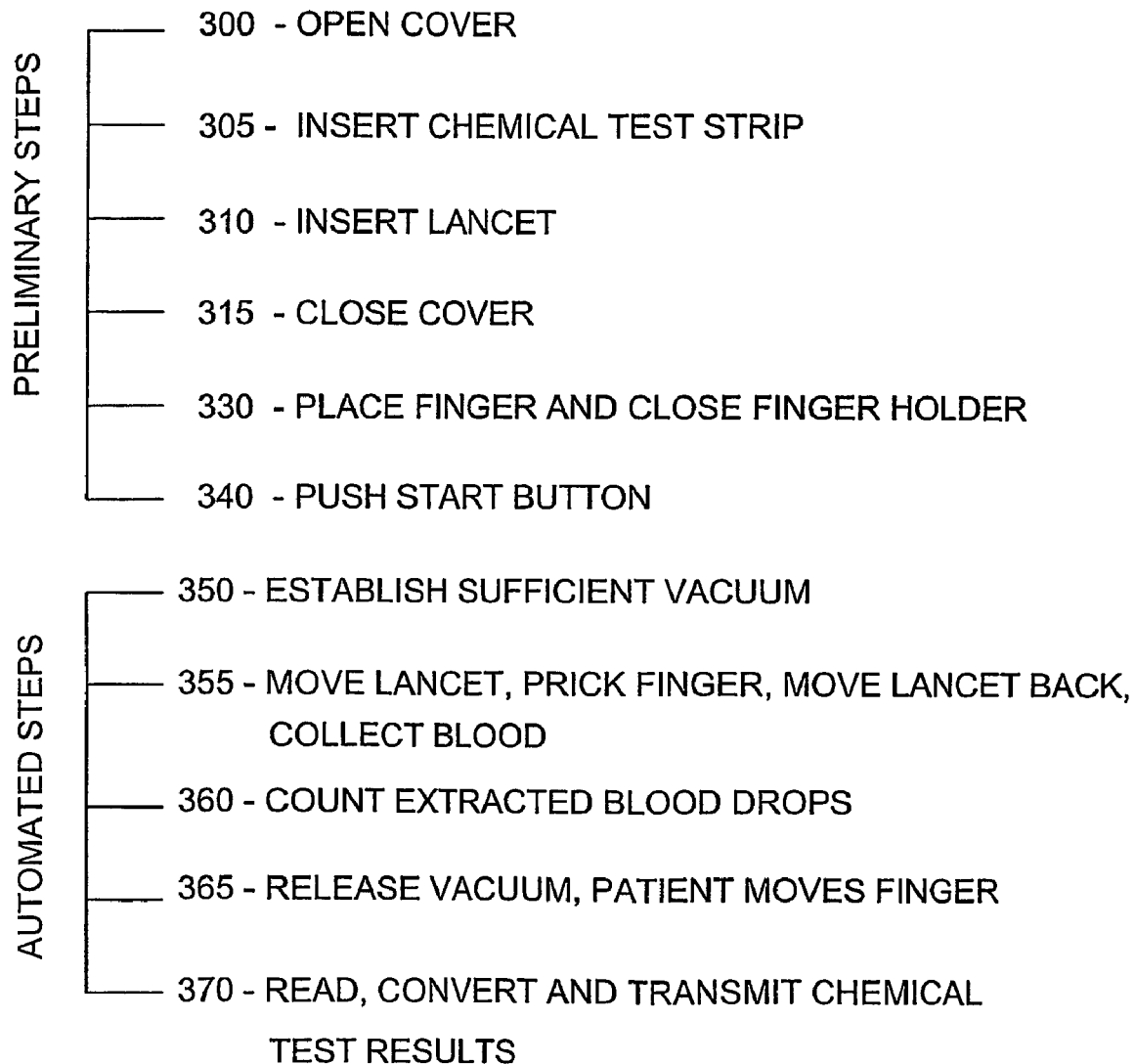
FIG. 4 is a flow chart of the main operational steps during use of the blood sampling and testing device of FIG. 1-3.

FIG. 4 is a flow chart of the main operational steps of the blood sampling and testing device of FIGS. 1 to 3. Operation begins with preliminary manual steps 300-315. A typical scenario for preliminary steps 300-315 may be as follows: the patient opens the cover 104 (step 300) and inserts a new single-use chemical test strip 148 into the chemical test strip holder 147 (step 305). The patient then inserts a sterile lancet 144 into the lancet holder 142 (step 310), and closes the cover 104 (step 315). It should be noted that step 310 may be carried out before step 305. It should also be noted that it is not mandatory to perform steps 300-315 as preliminary steps directly before steps 330-370 (i.e. blood sampling), although for sterilization reasons, it is recommended to do so.

The device 100 is ready for executing the subsequent blood sampling and testing when steps 300-315 are completed. When the patient is ready, he or she places a finger over the compartment 118, closes the finger holder 120 (step 330) and then pushes the pushbutton actuator 110 (step 350). This starts a sequence of steps 350-370, carried out automatically by device 100, as will now be explained.

The vacuum pump 160 establishes sufficient vacuum within the chamber 115 (step 350). In response, the motor 136 is activated causing the lancet 144 to move toward the patient's finger and prick it. The lancet 144 punctures the finger skin and creates a small incision. After pricking the finger, the motor causes the extracting unit to withdraw back into its original position so as not to collide with the blood drops after they are extracted from the finger during their downward fall on to the test strip 148.

The incision in the patient's finger that is created by the extracting unit is so small that blood cannot flow unless an external force is applied to release the blood: the vacuum achieves this by applying negative pressure, but in the absence of the vacuum, blood flow is prevented. Under vacuum conditions within the chamber 115, blood drops are drawn from the patient's finger; and fall on to the chemical test strip 148.

Whilst falling, the blood drops are sensed by the optical sensor 146 (step 360). When the desired number of blood drops is sensed, the disabling unit disables the action of vacuum pump 160 so that the vacuum is released and the patient is able to move her finger (step 365). As a consequence of the vacuum being released, blood flow ceases. Meanwhile, the chemical analysis process is executed by the chemical test strip 148. After a fixed interval of time (say a few minutes) the result of this test is indicated visually at the result window 152 and is read by the camera 182, converted to a suitable form by the electronic circuit 172 and transmitted to a remote unit. The operation of camera 182 and light source 145 are synchronized to illuminate result window 152 while the visual result is read.

According to one embodiment of the invention, device 100 may be coupled by a cable to a unit, which receives the visual test result and transmits it via a telephone line to a remote end to the physician of the tested patient.

According to another embodiment of the invention device 100 may be directly coupled to a telephone line for transmitting the imaged results to a remote end.

In the above embodiments, the disabling unit releases vacuum in response to the sensed number of drops. However, it is possible to release vacuum after a fixed time interval suitable for the collection of the desired amount of blood. The above-mentioned time interval may be measured, for example, from the moment of incision or from detection of the first blood drop to be collected by the chemical test strip. In either case, automatic operation can be manually interrupted if required by pushing the vacuum manual release button 124, thus releasing the vacuum and ceasing blood extraction.

According to the above embodiment of the invention, the device 100 can establish a fixed and sufficient vacuum level within chamber 115. However, it is possible to utilize the device 100 to establish several levels of vacuum. This creates the ability to control the rate of drop extraction by varying the vacuum level.

As exemplified above, the device 100 enables a patient to perform a self-blood test without the help of another person. However, it should be understood that the device 100 might be operated by another person, as long as the patient's finger is placed properly in the compartment 118. According to another embodiment of the present invention, the device 100 may be operable for successive tests on different people, for example, at a first aid station. In such an embodiment, the operation of the device 100 may or may not include step 370 (i.e., reading, converting and transmitting chemical test results).

Although in the above embodiment of the invention, a lancet cuts the skin, it should be understood that the cut might be accomplished by another means such as a laser or a blast of air.

According to another embodiment of the invention, the device 100 may be used for collecting blood for subsequent analysis rather than performing an immediate chemical test. According to this embodiment, the collecting receptacle does not require the chemical test strip 148.

The operation of the device 100 is not limited to extracting blood from a patient's finger, and any part of the human body wherein blood vessels are easy to reach may be suitable, providing that suitable suction can be applied to the organ from which blood is to be extracted. Moreover, the compartment 118 may be constructed in a way that enables placing one's whole finger inside.

Likewise, the device 100 is not limited to performing a chemical test on blood but can be utilized to perform different chemical tests on different body fluid samples. Thus, it is possible to perform chemical tests on urine or saliva by using a suitable chemical test strip and delivering the fluid sample through finger compartment 118.

It is also possible to perform an additional operational step in which the light source 145 and the camera 182 are activated respectively to illuminate and read the chemical test strip 148 at the beginning of the automated steps so that the device 100 identifies the chemical test to be performed and automatically adjusts the amount of fluid drops to be collected and the time interval between collecting the fluid and reading the result. In such case, the chemical test strip 148 may be encoded with an identity of the test associated therewith, for example by means of a barcode 175 or serial number. The disabling unit is responsively coupled to the electronic circuit 172 for control thereby, and the electronic circuit 172 is adapted to determine an identity of the chemical test strip and control the disabling unit accordingly. It will be understood that such adjustment can also be effected without the need of a camera so long as the electronic circuit 172 is able to determine the identity of the chemical test strip. Thus, in the case that a barcode is used to identify the chemical test strip, a barcode reader may be mounted inside the device for reading the barcode and conveying data indicative thereof to the electronic circuit.

The invention claimed is:

1. A blood extraction device for withdrawing a quantity of blood from a patient, said blood extraction device comprising:
   an incision unit for creating an incision in the patient;
   a release unit for urging blood drops to flow from said incision, and
   a disabling unit coupled to the release unit for disabling the release unit;
   a collecting receptacle disposed in spaced relationship with the release unit for collecting a predetermined plurality of discrete drops of blood that freely fall thereon from the incision without contacting any element of the device; and
   a drop counting unit disposed for counting blood drops flowing directly from the incision onto the receptacle and signaling only when the predetermined plurality of discrete drops of blood have been applied to said receptacle, wherein
   the disabling unit is adapted to disable the release unit automatically when the predetermined plurality of discrete drops of blood have been withdrawn.

2. The device according to claim 1, wherein the collecting receptacle comprises a single use chemical test strip on which the blood drops are gathered.

3. The device according to claim 2, further comprising:
   an imaging device for optically imaging the chemical test result obtained by the chemical test strip; and
   an electronic circuit coupled to the imaging device for transmitting data representative of an optical image of the result to a remote unit.

4. The device according to claim 2, wherein:
   the chemical test strip is visibly identified by a unique identity code,
   the disabling unit is responsively coupled to an electronic circuit for control thereby, and
   the electronic circuit is adapted to determine an identity of the chemical test strip and control the disabling unit accordingly.

5. The device according to claim 1, wherein the incision unit comprises a lancet.

6. The device according to claim 1, wherein the release unit comprises a vacuum unit.

7. The device according to claim 1, wherein the disabling unit comprises an electro-optical sensor for optically sensing the number of blood drops extracted.

8. A method for withdrawing a quantity of blood from a patient, said method comprising:
   creating an incision in the patient;
   urging blood drops to flow downwardly directly from said incision on to a collection receptacle disposed in spaced relationship with a release unit for collecting a predetermined plurality of discrete drops of blood that freely fall thereon from the incision without contacting any element of the device;
   counting the plurality of discrete drops of blood that flow downwardly directly from the incision to the receptacle; and
   inhibiting blood flow automatically when said predetermined plurality of discrete drops of blood have been withdrawn from the patient.

9. The method according to claim 8, wherein the receptacle is a single use test strip on which the drops of blood that flow from the incision are gathered.

10. The method according to claim 9, further comprising:
    optically imaging a test result obtained by the test strip; and
    transmitting data representative of an image of the result to a remote unit.

* * * * *

UNITED STATES PATENT AND TRADEMARK OFFICE
CERTIFICATE OF CORRECTION

PATENT NO. : 7,374,545 B2 Page 1 of 1
APPLICATION NO. : 10/496981
DATED : May 20, 2008
INVENTOR(S) : Yoram Alroy It is certified that error appears in the above-identified patent and that said Letters Patent is hereby corrected as shown below:

Title page of the patent, item Code (73), delete "(IS)" and insert therefor --(IL)--.

Signed and Sealed this

Twenty-eighth Day of October, 2008

JON W. DUDAS
*Director of the United States Patent and Trademark Office*